| United States Patent [19] | [11] | 4,294,117 |
|---|---|---|
| Buser et al. | [45] | Oct. 13, 1981 |

[54] SAMPLE CHARGER FOR A GAS CHROMATOGRAPH

[75] Inventors: Hansueli Buser, Arlesheim; Peter E. Jordi, Basel, both of Switzerland

[73] Assignee: Ciba-Geigy Corporation, Ardsley, N.Y.

[21] Appl. No.: 116,139

[22] Filed: Jan. 28, 1980

[30] Foreign Application Priority Data

Feb. 8, 1979 [CH] Switzerland .......................... 1243/79

[51] Int. Cl.$^3$ ........................................... G01N 31/08
[52] U.S. Cl. .................................................. 73/864.85
[58] Field of Search ................................... 73/422 GC

[56] References Cited

U.S. PATENT DOCUMENTS 4,084,440 4/1978 Carpenter et al. ............ 73/422 GC

Primary Examiner—S. Clement Swisher
Attorney, Agent, or Firm—Harry Falber

[57] ABSTRACT

A sample charger for a gas chromatograph has a charging chamber constructed for connection to the separating column of the gas chromatograph and receives a sample container in the form of a tube by the lengthwise insertion of a rod-shaped sample holder which comprises a hollow insertion tube, in which the sample container is releasably secured at its forward end. The charging chamber and insertion tube have carrier-gas inlet openings so that the interior of the insertion tube and the sample container can be scavenged with inert gas during the insertion process and, after the sample container has been completely inserted into the charging chamber, the carrier gas flows through the container into the separating column.

12 Claims, 1 Drawing Figure

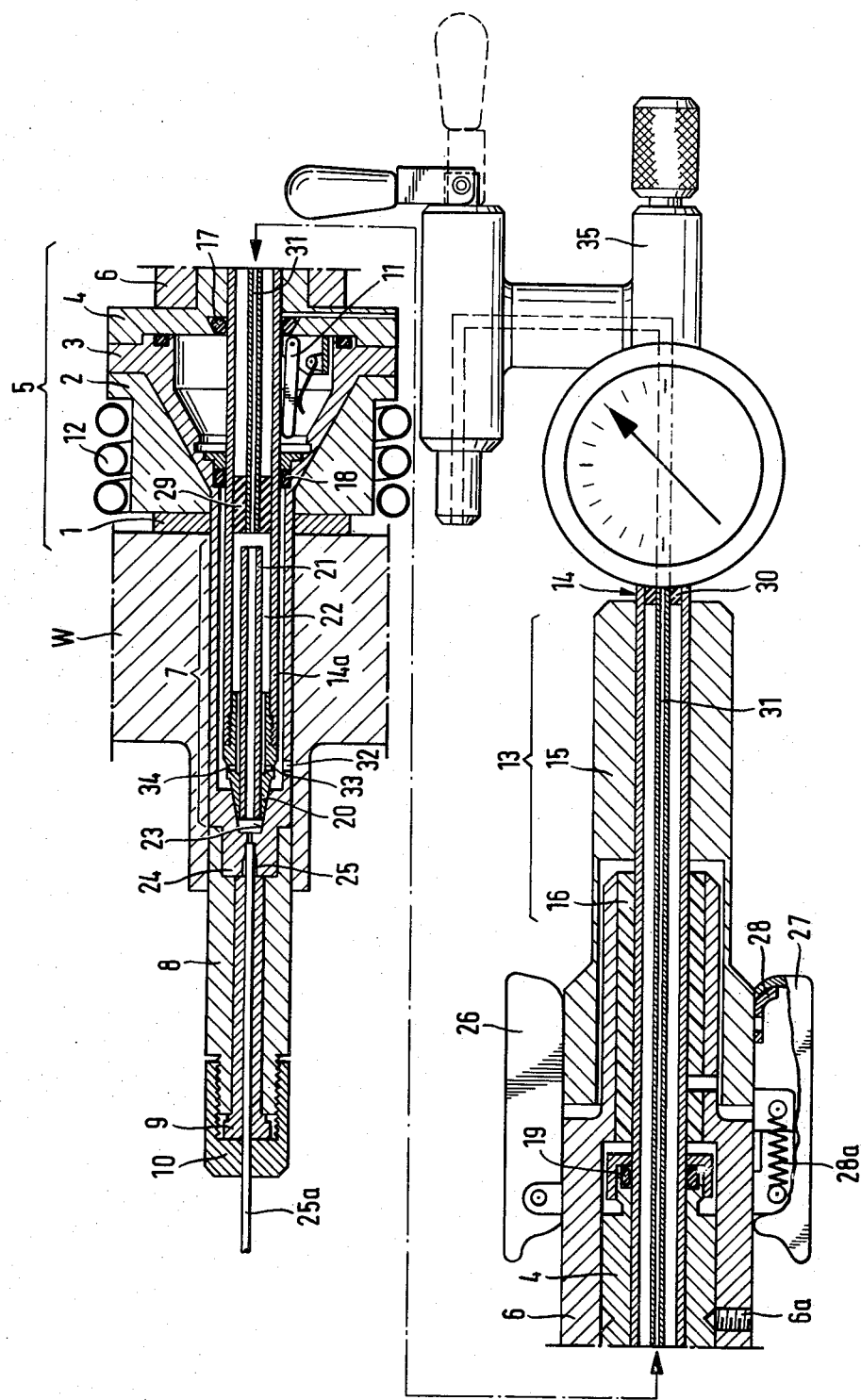

SAMPLE CHARGER FOR A GAS CHROMATOGRAPH

FIELD OF THE INVENTION

The invention relates to a sample charger for a gas chromatograph comprising a tubular desorption chamber having a connection at one end of the chamber for placing the interior thereof into communication with a gas chromatograph and being adapted to receive a substantially rod-shaped sample holder for introducing a sample container from the outside into the chamber.

Chemical monitoring of harmful substances in the air, for example in factories, laboratories and the like is becoming increasingly important. Gas chromatographic techniques are often employed for this purpose. In such processes, samples are collected in adsorption tubes by pumping the air under examination through the tube for a certain time, during which the components of interest accumulate on suitable adsorbent material in the tube. The thus-enriched components are then thermally desorbed from the adsorbent and analyzed by gas chromatography.

In gas-chromatographic analysis, it is essential to supply the sample correctly when inserting it into the gas-chromatographic separating column. One of the most important requirements is that the sample must be supplied under "inert" conditions, i.e. the adsorption tube must be free from air during desorption. This is advantageously achieved by scavenging with a suitable inert gas.

PRIOR ART

A sample charger for adsorption tubes now commonly used is described in "Gas-Chrom Newsletter", Volume 19, No. 2, March 1978 by Applied Science Laboratories Inc. However, this sample charger is not provided with a scavenging facility. Capsule-type sample chargers of this kind described e.g. in German Offenlegungsschrift No. 25 30 879 have proved to be satisfactory for introducing certain samples for gas chromatographic analysis. In these devices, a sample-holding capsule, firmly clamped to a rod-shaped holder, is introduced through a lock into a charging chamber and placed on a spike at the front end of the chamber. Known devices of this kind are simple, easy to handle and very advantageous in other respects, but unfortunately they are not suitable for use with adsorption tubes.

OBJECT OF THE INVENTION

An object of the invention is to provide a sample charger for a gas chromatograph which is suitable for charging adsorption tubes under inert conditions and which also is very simple to operate.

SUMMARY OF THE INVENTION

A sample charger in accordance with this invention preferably comprises in combination:

a tubular charging chamber for receiving a tubular container for the test sample;

connection means at one end of said charging chamber for placing the interior thereof into communication with the separating column of a gas chromatograph;

at least one inlet adjacent said one end of said charging chamber for the admission of a carrier gas thereinto;

a lock disposed adjacent the end of said charging chamber remote from said connection means, said lock including a lock gate operable to open or close said chamber to atmosphere;

a sample holder for introducing the tubular sample container from outside through said open lock gate and into said charging chamber, said sample holder including an open-ended insertion tube for lengthwise insertion into said charging chamber;

receiving means disposed at said one end of said charging chamber for receiving the leading end of said insertion tube in sealing engagement therewith and for placing the interior of said insertion tube in communication with the separating column of the gas chromatograph through said connection means;

holding means disposed at said leading end of said insertion tube for releasably holding the forward end of said tubular sample container within said insertion tube, said leading end of said insertion tube being sealed by the sample container held therein;

a passage between the inner wall of said insertion tube and the outer wall of said sample container held in said insertion tube for flow of carrier gas into the open end of said sample container remote from said holding means;

at least one inlet adjacent said leading end of said sample holder for the admission of carrier gas from said charging chamber into said passage; and releasable means for holding said insertion tube in sealing engagement with said one end of said charging chamber.

BRIEF DESCRIPTION OF THE DRAWING

A preferred embodiment of sample charger in accordance with the invention will now be described with reference to the single drawing which shows an axial section through the sample charger after the sample holder has been fully inserted.

DETAILED DESCRIPTION OF A PREFERRED EMBODIMENT

Referring to the drawing, the sample charger illustrated is disposed on an assembly plate 1 which secures it to a wall W of a gas chromatograph around an opening therethrough. On the forward side of the assembly plate 1 (i.e. on the left hand side thereof as viewed in the drawing), and located within the opening in the wall W, is a tubular charging chamber 7 for receiving the sample holder, generally designated 13 and to be described in greater detail hereinafter. The forward end 24 of chamber 7 is adjacent to a connecting member 8 for a gas chromatographic separating column 25a which passes through a plunger 9 and a screw-cap 10. As shown, the separating column 25a is preferably a capillary.

On the side of the assembly plate 1 remote from the chromatograph is a lock, generally designated 5. Lock 5 comprises three housing parts, respectively designated 2, 3 and 4, and in the illustrated embodiment the central housing part 3 is integral with the tubular charging chamber 7. A lock valve or gate 11 is disposed in lock 5 and when in the closed position (not shown in the drawing), with the sample holder 13 withdrawn, seals the mouth of the chamber 7 from the atmosphere via an O-ring 18.

A guide sleeve 6 for the sample holder 13 is disposed on a rearward tubular extension of the outer housing part 4, and has a connection 6a for scavenging gas. Rearwardly of the housing part 4, the sleeve 6 has a portion of reduced external diameter which is lined with a PTFE insert 16. A cooling coil 12 is disposed around the inner housing part 2 of the lock 5.

The arrangement so far described corresponds in principle with the capsule-type sample charger disclosed in German Offenlegungsschrift No. 25 30 879 supra.

The sample holder 13 essentially comprises an open-ended insertion tube force-fitted into a handle 15. For convenience, the forward part of the insertion tube is designated 14a. When inserted, as shown in the drawing, the insertion tube 14 is received by the guide sleeve 6, and passes through open lock gate 11 into chamber 7. The insertion tube 14 in its inserted position is sealed by O-rings 17 and 19.

Holding means in the form of a screw-threaded nipple 20 are disposed at the front or chamber end 14a of insertion tube 14. Nipple 20 receives the forward end of a sample-containing adsorption tube 21 to hold it at the forward end of the insertion tube within the chamber 7, so as to leave a gap or annular passage 22 between tube 21 and the inner wall of tube 14 or the rear portion of the nipple. Adsorption tube 21 is open at both ends and its front portion and the front portion of the inner surface of nipple 20 are both slightly conical, to ensure a good fit. In its received position, the front end-face of tube 21 is flush with the front end-face of nipple 20.

The outer surface of nipple 20 has a conical ground surface and engages to give a tight seal with receiving means formed by a complementary conical ground surface 23 in the front wall 24 of chamber 7. Spherical ground surfaces or other sealing means could be provided instead of conical surfaces.

The front end 24 of chamber 7 is formed with connection means for placing the chamber and separating column into communication in the form of a bore 25 disposed so that the separating column 25a held by the screw cap 10 can be conveyed by the plunger 9 practically up to the mouth of the adsorption tube 21, thus greatly reducing the dead space between the sample tube 21 and the beginning of the column.

In order to ensure efficient but releasable sealing engagement between nipple 20 and the front end 24 of the chamber 7 during operation, sample holder 13 is resiliently pressed axially and inwardly by two spring gripping levers 26 and 27. The two levers, which are pivoted to sleeve 6 and have springs 28a, are of any known kind and engage corresponding lugs 28 on handle 15.

The front of the handle 15 is constructed so that it exactly fits on the reduced diameter part of the guide sleeve 6. A groove and tenon combination on the handle and guide sleeve (not shown) is used to ensure that the handle, and consequently the insertion tube and nipple, connot rotate after the insertion tube has been completely inserted. This is to prevent damage to the very accurate conical ground surfaces on the nipple and in the front wall of the desorption chamber.

A capillary 31 is coaxially secured by two spacers 29, 30 in the interior of tube 14 to the rear of the sample tube 21. Capillary 31 acts as a restrictor and also connects the interior of the front part 14a of tube 14, in front of the forward spacer 29, to atmosphere. A pressure-regulating valve 35 or the like is connected to the outer end of capillary 31 for adjustment of the restrictor.

Chamber 7 has a carrier-gas inlet or connection 32 slightly along from its end 24. At the same distance (when tube 14 is in the completely inserted position) are two carrier-gas inlet openings 33, 34 in nipple 20 which communicate with the annular space 22 between tube 21 and the inner wall of the nipple.

In order to insert a sample into the gas chromatograph, the slightly conical end of sample tube 21 is inserted into nipple 20, which is then screwed onto the front end 14a of the insertion tube 14. As in the known capsule charging devices, the sample is then inserted by the sample holder through sleeve 6 and lock 5 into desorption chamber 7. During the insertion process, carrier gas is desirably supplied through inlet 32 and flows through the sample tube and valve 35 to the atmosphere, thus automatically scavenging the sample tube. The pressure during the insertion operation can be kept constant by suitably adjusting the valve or the restrictor. Annular space or passage 22 is simultaneously scavenged. After the insertion process is complete and nipple 20 is in tightly sealed engagement with front end 24, the carrier gas flows through opening 33 and 34 into space 22 and thence through sample tube 21 and bore 25 into the separating column.

Thus, it will be seen that, with the sample charger of this invention, both the sample tube and the surrounding cavities can be automatically scavenged with carrier gas during the insertion process, whereby the sample is supplied under inert conditions, in accordance with the best practice. No complicated manipulation is required for this purpose; it is only necessary, as in the known capsule systems, to insert the sample-holder and secure it by the gripping levers.

We claim:

1. A sample charger for introducing a test sample into a separating column of a gas chromatograph, comprising in combination:

a tubular charging chamber for receiving a tubular container for the test sample;

connection means at one end of said charging chamber for placing the interior thereof into communication with the separating column of a gas chromatograph;

at least one inlet adjacent said one end of said charging chamber for the admission of a carrier gas thereinto;

a lock disposed adjacent the end of said charging chamber remote from said connection means, said lock including a lock gate operable to open or close said chamber to atmosphere;

a sample holder for introducing the tubular sample container from outside through said open lock gate and into said charging chamber, said sample holder including an open-ended insertion tube for lengthwise insertion into said charging chamber;

receiving means disposed at said one end of said charging chamber for receiving the leading end of said insertion tube in sealing engagement therewith and for placing the interior of said insertion tube in communication with the separating column of the gas chromatograph through said connection means;

holding means disposed at said leading end of said insertion tube for releasably holding the forward end of said tubular sample container within said insertion tube, said leading end of said insertion tube being sealed by the sample container held therein;

a passage between the inner wall of said insertion tube and the outer wall of said sample container held in said insertion tube for flow of carrier gas into the open end of said sample container remote from said holding means;

at least one inlet adjacent said leading end of said sample holder for the admission of carrier gas from said charging chamber into said passage; and releasable means for holding said insertion tube in sealing engagement with said one end of said charging chamber.

2. A sample charger as defined in claim 1, including means for controlling the pressure of carrier gas flowing through said charging chamber into the gas chromatograph.

3. A sample charger as defined in claim 2, wherein said pressure controlling means include a restrictor disposed in said insertion tube behind said sample container, said restrictor serving also to connect the interior of said sample holder to atmosphere.

4. A sample charger as defined in claim 1, wherein said receiving means in said charging chamber for receiving said insertion tube comprise conical or spherical sealing surfaces formed in said one end of said charger and complementary sealing surfaces formed on said leading end of said insertion tube.

5. A sample charger as defined in claim 1, wherein said holding means for said sample container comprises a nipple which is releasably secured to said leading end of said insertion tube.

6. A sample charger as defined in claim 5, wherein said at least one inlet for the admission of carrier gas into said passage is formed in said nipple.

7. A sample charger as defined in claim 1, wherein said charging chamber and said lock together form a structure which can be connected to or released from a gas chromatograph as a single unit.

8. A sample charger as defined in claim 1, wherein said releasable means for holding said insertion tube and charging chamber in engagement include resilient gripping levers.

9. A sample charger as defined in claim 1, including means for preventing the sample holder from rotating around its longitudinal axis before said receiving means in said charging chamber are engaged by said insertion tube.

10. A sample charger as defined in claim 1, wherein said insertion tube receiving means and said gas chromatograph connection means are constructed to permit said forward end of said sample container to be brought closely adjacent the mouth of the separating column of the gas chromatograph.

11. A sample holder for introducing a tubular sample container into the tubular charging chamber of a gas chromatograph, comprising in combination an open-ended insertion tube adapted for lengthwise insertion into said charging chamber;

a sealing surface formed on one end of said insertion tube for sealing engagement with a complementary sealing surface on the front end of said charging chamber;

holding means disposed at said one end of said insertion tube for releasably holding the forward end of said tubular sample container within said insertion tube, said one end of said insertion tube being sealed by the sample container held therein;

at least one inlet for the admission of carrier gas adjacent said one end of said insertion tube;

a passage between the inner wall of said insertion tube and the outer wall of said sample container held in said insertion tube for flow of carrier gas from said inlet into the open end of said sample container remote from said holding means; and a restrictor in said insertion tube disposed behind said sample container for controlling the pressure of carrier gas passing through said passage into said sample container, said restrictor defining an outlet communicating the interior of said insertion tube with the atmosphere.

12. A sample holder as defined in claim 11, including a valve for adjusting said restrictor.

* * * * *